United States Patent
Uhrenius et al.

(10) Patent No.: US 6,850,800 B1
(45) Date of Patent: Feb. 1, 2005

(54) EVOKED RESPONSE DETECTOR, AVERAGING THE VALUE OF THE AMPLITUDE OF THE PICKED-UP ELECTRODE SIGNAL

(75) Inventors: Åsa Uhrenius, Stockholm (SE); Berit Larsson, Danderyd (SE); Göran Budgifvars, Spånga (SE); Feresteh Shojaei, Solna (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/719,740

(22) Filed: Apr. 18, 2001

(51) Int. Cl.[7] ................................................. A61N 1/37
(52) U.S. Cl. ........................................... 607/27; 607/28
(58) Field of Search ............................. 607/27, 28, 9, 607/7; 600/510

(56) References Cited

U.S. PATENT DOCUMENTS

| 4,757,815 A | 7/1988 | Strandberg et al. | |
| 4,913,146 A * | 4/1990 | DeCote, Jr. | 607/9 |
| 5,391,192 A | 2/1995 | Lu et al. | |
| 5,417,718 A | 5/1995 | Kleks et al. | |
| 5,458,623 A | 10/1995 | Lu et al. | |
| 6,238,419 B1 * | 5/2001 | Lindgren | 607/9 |

FOREIGN PATENT DOCUMENTS

EP  0 836 867  4/1998

* cited by examiner

Primary Examiner—Jeffrey R. Jastrzab
(74) Attorney, Agent, or Firm—Schiff Hardin LLP

(57) ABSTRACT

A heart stimulator has a pulse generator which emits stimulation pulses for delivery to the heart of a patient through a lead connected to the pulse generator and introduced into the heart. The heart stimulator has an evoked response detector which includes a measuring unit for measuring electrode signals picked up by the lead. An averaging unit is supplied with the electrode signals and forms an average value of the amplitude of the respective electrode signals for each heartbeat. A comparator in the evoked response detector compares the average value for each heartbeat with two predetermined limit values and emits a signal indicating that the electrode signal results from a fusion beat if the average values are between the two limit values.

8 Claims, 4 Drawing Sheets

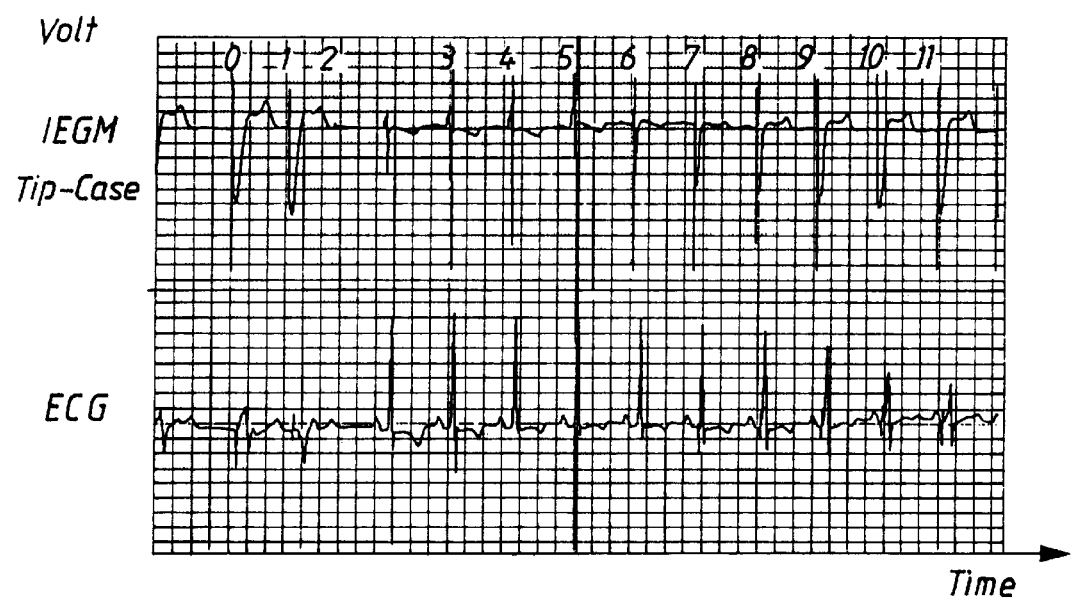
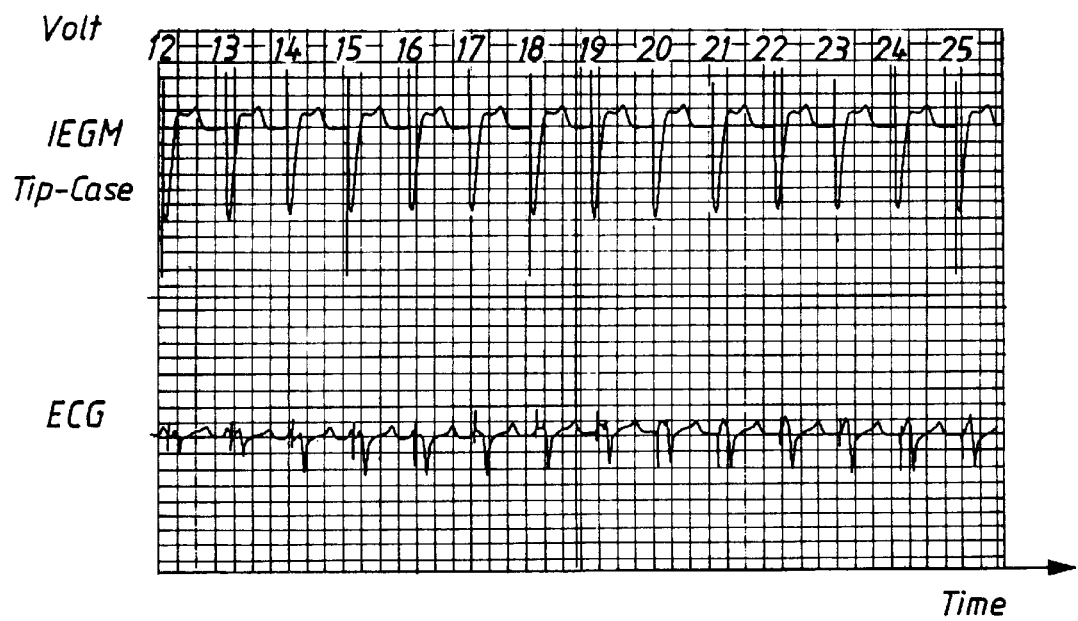

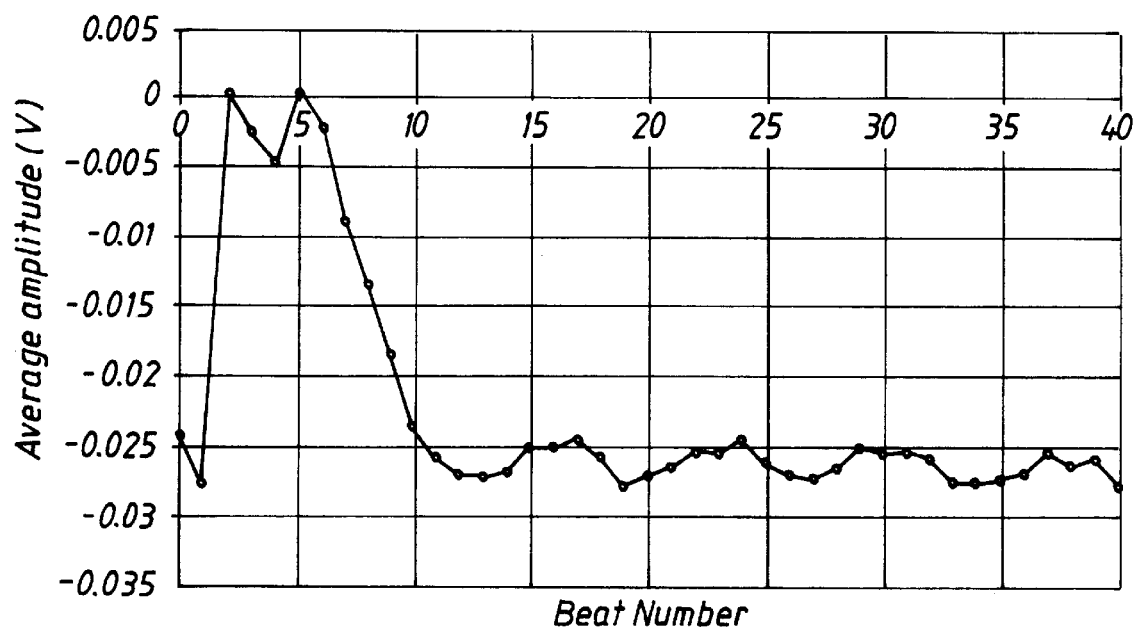
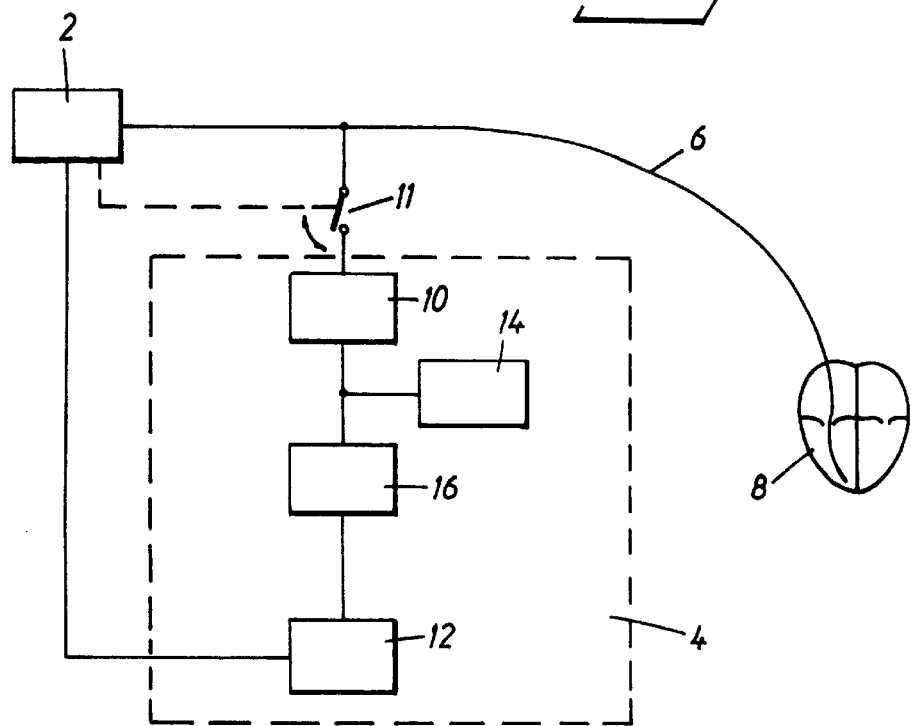

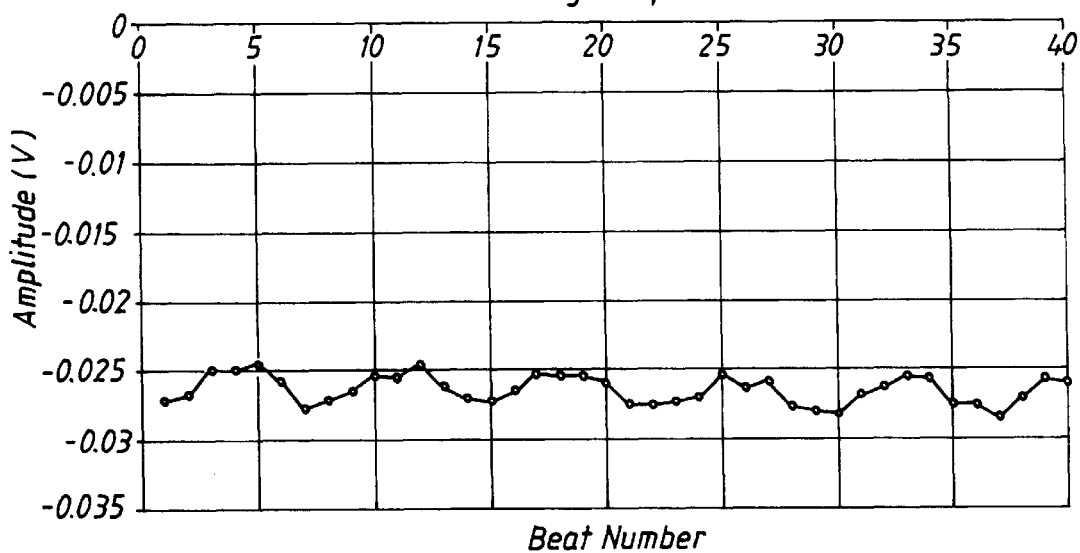
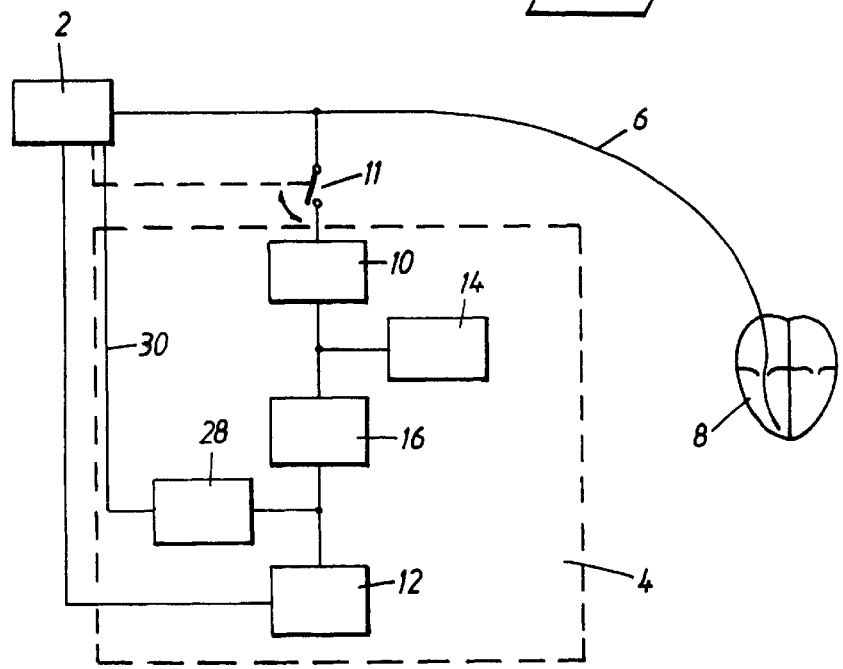

EVOKED RESPONSE DETECTOR, AVERAGING THE VALUE OF THE AMPLITUDE OF THE PICKED-UP ELECTRODE SIGNAL

BACKGROUND OF THE INVENTION

1. Field of the Invention

The present invention relates to an evoked response detector for a heart stimulator, the heart stimulator having a pulse generator for producing stimulation pulses for delivery to the heart of a patient through a lead intended to be connected to the pulse generator and introduced into the heart, the evoked response detector having measuring means for measuring electrode signals picked up by the lead.

2. Description of the Prior Art

To reduce the energy consumption of heart stimulators, an automatic threshold search function, a so called AUTOCAPTURE™ function, is used to maintain the energy of the stimulation pulses at a level just above that which is needed to effectuate capture; cf. e.g. U.S. Pat. No. 5,458,623. A reliable detection of the evoked response, which then is necessary, is, however, not a simple matter, especially when it is desired to sense the evoked response with the same electrode as the one delivering the stimulation pulse and in particular if the sensing is performed by a unipolar electrode configuration.

Currently, fusion beats create a significant problem for the AUTOCAPTURE™ function since these beats often are not detected as heart beats. Instead the heart stimulator in question interprets the evoked response as a loss of capture and as a consequence a backup pulse is issued and the stimulation pulse amplitude is increased. After several such undetected fusion beats the heart stimulator will be in a high output mode, where it remains until the next threshold search is performed. This misinterpretation by the heart stimulator of the evoked response signal will, of course, increase the current drain and decrease the lifetime of the battery and the AUTOCAPTURE™ function will be disabled for some time.

In European Application 0 836 867 a heart stimulating device for avoiding fusion beats is disclosed. Thus, a technique is described for improved detection of intrinsic events. A control means is then activating a non-filtered sensing means before the end of a basic escape interval and is prolonging this escape interval by a predetermined length if the non-filtered sensing means senses a QRS complex, such that the corresponding filtered signal, which is delayed due to the filtering procedure, has time to reach the control means for safe verification of the sensed QRS complex.

In U.S. Pat. No. 4,757,815 is disclosed a heart pacemaker including a pulse generator and a circuitry for measuring a respiration signal of a patient and a control unit for controlling the pulse generator by changing the pulse repetition rate dependent on the respiration signal. In this known device a series of heart action signals are acquired by e.g. a QRS-detector. The amplitudes (R-waves) of the heart action signals are subject to fluctuations caused by the respiration cycle of the user of the heart pacemaker. The respiration measurement is undertaken by measuring, for each QRS-complex, the distance between the most positive point and the most negative point of the complex, whereas the distance variation between consecutive measurements being a measure of the respiration of the patientAccording to this known device two separate points of the QRS-complex must be identified and determined, this is achieved by a peak sensing means including sample and hold circuits.

In U.S. Pat. No. 5,391,192 is disclosed a clinical programming system for use with an implanted cardiac system to automatically determine the minimum energy required to evoke a ventricular depolarization. Evoked response is detected through evaluation of the integral of R-waves provided by a surface electrocardiogram. U.S. Pat. No. 5,391,192 makes no attempt to differentiate between fusion beats and true captured beats.

SUMMARY OF THE INVENTION

An object of the present invention is to provide an improved evoked response detector for a heart stimulator which makes reliable detection of fusion beats for a unipolar sensing electrode configuration.

An additional object of the present invention is to provide, in addition to the fusion beat detection, a possibility to determine the respiration rate of the patient from the detected signal.

The above object is achieved in accordance with the principles of the present invention in a heart stimulator having a pulse generator which emits stimulation pulses for delivery to the heart of a patient through a lead connected to the pulse generator and introduced into the heart, and an evoked response detector having a measuring unit for measuring electrode signals picked up by the lead, an averaging unit which forms an average value of the amplitude of the respective picked-up electrode signals for each heartbeat, and a comparator which determines whether a pick-up electrode signal results from a fusion beat by comparing the average value with two different predetermined limit values. The evoked response signals are determined to result from fusion beats if the average values are within the interval between the two limit values.

With the detector according to the invention reliable detection of fusion beats is possible with low as well as high polarizing unipolar leads, which is an important advantage since unipolar leads are less complicated to manufacture and have longer working life than bipolar electrodes.

In one embodiment of the detector according to the invention the measuring unit is adapted to determine the DC level of the measured electrode signals and subtract this DC level from each sample, and the averaging unit forms the average value of the samples from the evoked response time window to form the average value of the amplitude of the measured electrode signals. It is important to subtract the DC level from the measured electrode signal to get a corrected electrode signal for a subsequent analysis.

In a further embodiment of the evoked response detector according to the invention, a respiration signal determining means is arranged, whereby a respiration signal, representing the respiration rate of the patient, is determined, from a predetermined number of said average values from a predetermined number of heart cycles by the respiration signal determining means.

DESCRIPTION OF THE DRAWINGS

FIG. 1 shows a unipolar IEGM and ECG recorded during experiments on an animal.

FIG. 2 shows the average amplitudes obtained from the IEGM in FIG. 1 analyzed by the detector according to the invention.

FIG. 3 is a block diagram of the principal layout of the heart stimulator according to the invention.

FIG. 6 shows a the average amplitudes obtained from the IEGM in FIG. 5 analyzed by the detector according to the invention.

FIG. 7 is a block diagram of the principal layout of the heart stimulator according to a second advantageous embodiment of the invention.

DESCRIPTION OF THE PREFERRED EMBODIMENTS

Figure 4:
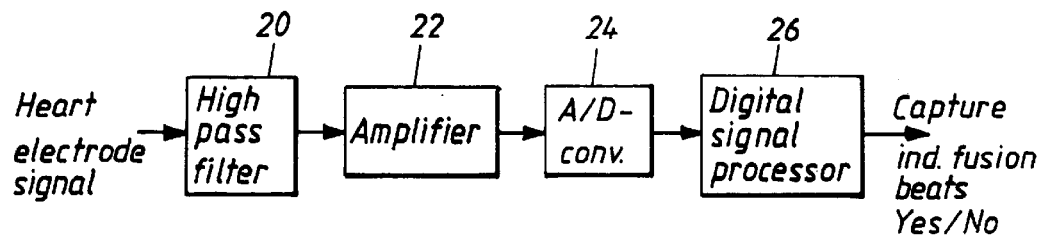
FIG. 4 is a block diagram of an embodiment of the evoked response detector according to the invention.

FIG. 1 shows a unipolar IEGM, measured between electrode tip and the casing of the heart stimulator, and the ECG, recorded during experiments on an animal. The recorded heart beats are numbered from 0 to 25.

Beats number 0 and 1 represent two completely stimulated captures.

In the experiments an external pacemaker, operated in VVI mode, was used, but due to the very long blind detection window of approx. 40 msec before the stimulation pulse, the pacemaker has not been inhibited by the intrinsic beats. Accordingly pseudofusion beats have appeared, see beats No. 3, 4, 5, and 6. For these beats stimulation would have been inhibited by a commercially available implantable pacemaker. In the present experiments, however, these beats are interpreted as losses of capture. The sixth beat is the first beat which is somewhat stimulated, but the intrinsic part is much more pronounced than the stimulated one and this beat would probably have been detected by the QRS detector in a commercially available pacemaker.

Beats No. 7, 8, 9, and 10 are fusion beats. The following beats No. 11–25 are only stimulated heart beats.

In FIG. 2 the average amplitude values of the recorded IEGM are shown for each of the heart beats (and also for subsequent heart beats up to heart beat No. 40). These average amplitude values are determined by the evoked response detector according to the invention as will be described below.

As can be seen from FIG. 2 completely stimulated captures result in a comparatively large negative average amplitude, cf. heart beats 0, 1 and 12–40.

For the pseudofusion beats 3, 4, 5, and 6 a low negative or zero average amplitude is measured in the experiments, which is interpreted as losses of capture.

For the fusion beats 7, 8, 9, and 10 the average amplitudes are situated between the measured average amplitude for pseudofusion beats and the amplitude for the completely stimulated beats. The absolute values of the average amplitudes of these fusion beats are continuously increasing from beat 7 to beat 10 due to the fact that the beats become more and more stimulated.

From these experiments and this analysis it has been found that by setting appropriate limit values for the average amplitudes of the measured electrode signals, capture, including fusion beats, and loss of capture can be detected with the detector according to the invention. Thus for the specific example explained with reference to FIGS. 1 and 2 an average amplitude exceeding –0.005 V could be interpreted as loss of capture, and an average amplitude below –0.005 V as capture, average amplitudes between –0.005 V and –0.022 V being interpreted as fusion beats.

FIG. 3 shows a block diagram of the principal layout of the heart stimulator according to the invention. The stimulator includes a pulse generator 2 which through a lead 6 is connected to the heart 8 of a patient. The pulse generator 2 is devised to produce stimulation pulses of varying amplitudes which through the lead 6 are transferred to the heart 8. The evoked response detector 4 of the heart stimulator is also connected to the lead 6.

The evoked response detector 4 has a filter and measuring unit 10. The filtered electrode signal is supplied to an averaging unit 16 and to comparator 12 for distinguishing capture also for fusion beats and losses of capture by comparing the average amplitudes obtained from the averaging unit 16 with suitably selected limit values as described above in connection with FIG. 2.

The filter and measurement means 10 is disconnected by the switch 11 from the lead 6 during stimulation.

A timer 14 is provided for determining an evoked response time window during which the electrode signal is measured and stored. This evoked response window normally extends from 15 to 55 msec after stimulation.

Thus after a blanking time of about 15 msec the measured electrode signal (IEGM) is sampled and digitized during this evoked response window, and the mean value of these samples is formed. This procedure is performed in the averaging unit 16, which thus supplies to the comparator 12 an average amplitude value for each heart beat. A suitable sampling frequency can be e.g. 512 Hz, which results in about 20 samples per beat.

To obtain a reliable result it is also desirable to eliminate any DC level in the measured electrode signal (IEGM). This can be performed by sampling the measured IEGM signal before the emission of a stimulation pulse and forming a mean value of these samples. This mean value represents the DC level and is subtracted from each sample of the subsequent measured electrode signal.

FIG. 4 shows in more detail one embodiment of the evoked response detector according to the invention. The heart electrode signal picked up by the lead 6 in FIG. 3 is then supplied to a highpass filter 20. An amplifier 22 and an A/D converter 24 are provided for amplifying and A/D converting respectively the filtered signal. A digital signal processor 26 calculated the average amplitudes of the measured electrode signals and compares them with suitably selected limit values as described above.

Thus in the embodiment shown in FIG. 4 the algorithm for distinguishing between capture also for fusion beats, and loss of capture is implemented in software by use of a microprocessor. Instead of a microprocessor this algorithm can also be implemented in random logic, which means realization by ordinary logic element, that is logic gates.

The detector according to the invention can also be implemented in the heart stimulator electronics by use of switch capacitor (SC) technique. The algorithm is then implemented in SC technique, where different capacitors serve as memory elements for storing the different electrode potentials and SC-adding, subtracting and multiplying circuits are used for performing the necessary calculations as explained above.

Figure 5:
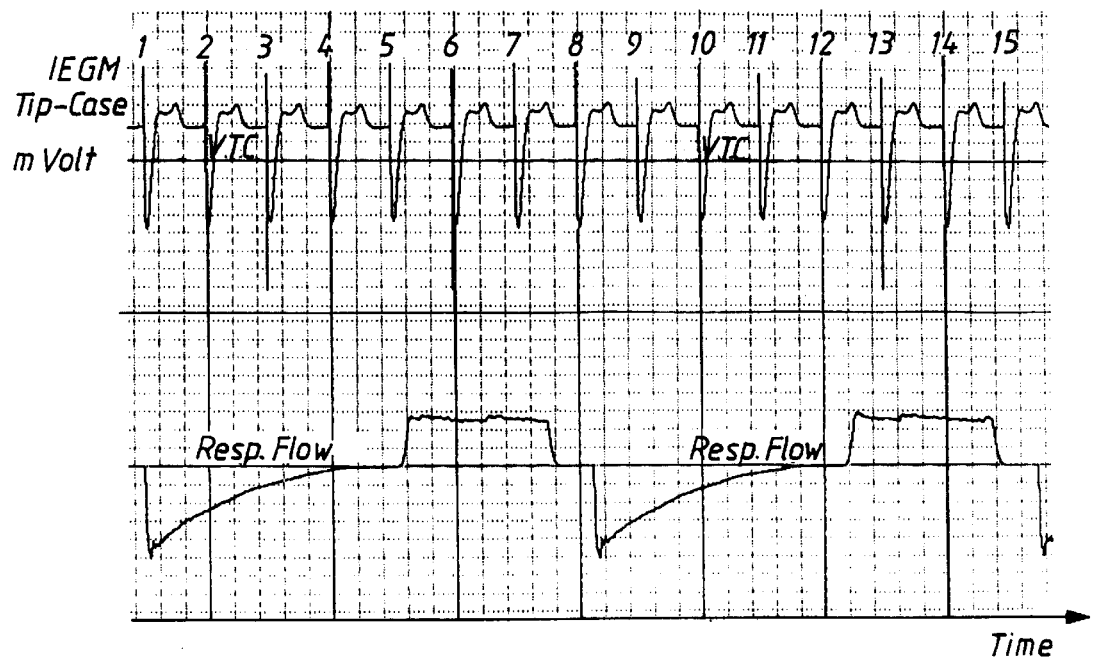
FIG. 5 shows a unipolar IEGM and a curve showing the respiration flow recorded during experiments on an animal.

FIG. 5 shows a unipolar IEGM and a curve showing the respiration flow recorded during experiments on an animal. In the IEGM curve an amplitude variation can be seen corresponding to the respiration flow.

FIG. 6 shows the average amplitudes obtained from the IEGM in FIG. 5 and analyzed by the detector according to the invention. The amplitude variation in dependence of the respiration can clearly be seen. As can be seen from the figure a respiration cycle comprises approximately 6–9 average values.

FIG. 7 is a block diagram of the principal layout of the heart stimulator according to a second advantageous embodiment of the invention.

This embodiment includes, in addition to the embodiment described in relation to FIG. 3, a respiration signal determining unit 28 supplied with the average values generated by the averaging unit 16. The respiration signal determining unit 28 generates a respiration signal 30, representing the respiration rate of the patient, from a predetermined number of said average values. The respiration signal 30 is applied to the pulse generator 2 where it is used as a control signal for controlling the stimulation rate in accordance with a respiration rate responsive algorithm. Using the respiration rate to control the stimulation rate of a pacemaker is well known the to a person skilled in the art of pacemakers, cf. e.g. U.S. Pat. No. 4,702,253 and is therefore not described herein.

Although modifications and changes may be suggested by those skilled in the art, it is the intention of the inventors to embody within the patent warranted hereon all changes and modifications as reasonably and properly come within the scope of their contribution to the art.

What is claimed is:

1. A heart stimulator comprising:

a pulse generator which emits stimulation pulses;

a lead connected to said pulse generator and adapted for introduction into a heart for delivering said stimulation pulses to cardiac tissue; and an evoked response detector having a measuring unit connected to said lead for measuring electrode signals picked up by said lead, said electrode signals having an amplitude, an averaging unit supplied with said electrode signals and forming an average value of the respective amplitudes of the electrode signals for each heartbeat, and a comparator supplied with said average values for comparing said average values with two different predetermined limit values, said comparator emitting a comparator output indicating an electrode signal arising from a fusion beat if said average values are between said two limit values.

2. A heart stimulator as claimed in claim 1 wherein said measuring unit samples and digitizes said electrode signals within a predetermined evoked response time window, starting at a predetermined time following emission of a stimulation pulse by said pulse generator.

3. A heart stimulator as claimed in claim 2 wherein said measuring unit determines a d.c. level of said electrode signals and subtracts said d.c. level from each sample, and wherein said averaging unit forms an average value of the samples in the time window to form said average value of the amplitudes of the respective electrode signals for each heartbeat.

4. A heart stimulator as claimed in claim 2 wherein said measuring unit has a sampling frequency, and wherein said evoked response window has a duration, so that approximately twenty samples are obtained from each electrode signal.

5. A heart stimulator as claimed in claim 1 wherein said lead is a unipolar lead.

6. A heart stimulator as claimed in claim 1 further comprising a respiration signal determining unit for identifying a respiration signal, representing a respiration rate of the patient, from a predetermined number of said average values.

7. A heart stimulator as claimed in claim 6 wherein said respiration signal determining unit determines said respiration signal from a variation of the amplitudes of said predetermined number of average values.

8. A heart stimulator as claimed in claim 7 further comprising a control unit for controlling a stimulation rate of said pulse generator, and wherein said respiration signal determining unit supplies said respiration signal to said control unit for controlling said stimulation rate.

* * * * *